United States Patent [19]

Capps

[11] Patent Number: 5,372,935
[45] Date of Patent: Dec. 13, 1994

[54] DETECTION OF CANDIDA

[75] Inventor: Charles L. Capps, Little Rock, Ark.

[73] Assignee: Pearl Medical Science, Inc., Little Rock, Ark.

[21] Appl. No.: 84,858

[22] Filed: Jun. 29, 1993

[51] Int. Cl.$^5$ .......................... C12Q 1/04; C12N 1/16; G01N 33/48

[52] U.S. Cl. .................... 435/34; 435/255.4; 435/63

[58] Field of Search ............ 435/34, 7.31, 253.6, 435/254, 255, 260, 29, 255.4; 436/63, 166

[56] References Cited

U.S. PATENT DOCUMENTS 3,880,717  4/1975  Rubin et al. .................. 195/112
4,581,223  4/1986  Kass .............................. 424/3
4,766,063  8/1988  Boussemaer .................... 435/5

OTHER PUBLICATIONS

Torres-Bauza et al. "Protoplasts from Yeast and Mycelial Forms of *Candida albicans*" 1908, pp. 341–349.
Partridge et al. "Candida Protoplasts and Their Ultrastructure" 1974 pp. 166–178.

Primary Examiner—James C. Housel
Assistant Examiner—N. Bhat
Attorney, Agent, or Firm—Jack A. Kanz

[57] ABSTRACT

An alkaline solution containing a complex of $C_{30}H_{31}ClN_6$ is used as a specific indicator for detecting the presence of Candida spp. When Candida yeast bodies are introduced into the indicator solution, the yeast bodies are stained and form a blue or violet precipitate.

7 Claims, No Drawings

DETECTION OF CANDIDA

This invention relates to detection of Candida. More particularly, it relates to materials and methods for detecting and providing immediate colorimetric indication of the presence of as well as representative infection levels of resident colonies of Candida, particularly *C. albicans* and *C. tropicalis*.

BACKGROUND OF THE INVENTION

Although many fungal genera have been identified as etiologic opportunistic infections, it is known that Candida. constitute the majority of the pathogens involved in these infections. Candida is unique among opportunistic pathogens because it is a resident fungus found in the normal flora of mucosa and skin of many animals, including humans. Although there are numerous species of Candida, the majority of infections are caused by *C. albicans* and *C. tropicalis*.

Immunosuppression, wherein fungal growth attains rapid and extensive colonization, is attributable to numerous causes, some of which are lifestyle related. It is known, for example, that changes in flora pH increases the likelihood of Candida growth. Fermentation of resident lactobacilli, with the subsequent formation of acid, favors yeast growth, Additionally, pregnancy and diabetes may incite growth since the level of glycogen increases in the vagina. Broad spectrum antibiotics causing changes in flora are probably the greatest contributing factor in observational increases of Candida infections. Lifestyle clothing has been given much consideration because restrictive, non-aerable garments are commensal in incubation of fungal genera. Additionally, commonly-used feminine hygiene products may contribute to the condition.

Laboratory diagnosis is currently the accepted and most definitive method for determining the presence of infection levels of Candida. However, these methods are time-consuming because they generally require culturing, sub-culturing and clinical evaluation. Therefore, the patient and physician are relegated to simply collecting a sample and waiting while the sample is submitted to a clinical laboratory for appropriate diagnosis. Although methods for colorimetric determination of Candida exist, these procedures still require extended time for culturing prior to the diagnosis. Accordingly, a time period of approximately forty-eight (48) hours is required for diagnostic evaluation using conventional methods.

SUMMARY OF THE INVENTION

The present invention permits rapid detection and evaluation of Candida yeast bodies without employing culturing, incubation, sub-culturing or microscopic examination. In accordance with the invention, a specimen is collected and introduced into a solution containing a specific indicator which is selectively responsive to the presence of Candida yeast bodies. Within minutes after exposure to the indicator, Candida yeast bodies assume a distinct color and appear as a violet-colored suspension of precipitate in the solution. The color can be concentrated and the relative amount of Candida bodies can be determined by centrifuging the solution. Color density and speed of formation are indicative of Candida concentration. Because of simplicity of use and immediate indication, the method of the invention may be self-administered or physician-administered by simply collecting a specimen; introducing the specimen into an alkaline solution containing specific indicator; allowing the indicator to mark the fungal bodies; and observing the color change representative of the presence of Candida yeast bodies.

DESCRIPTION OF THE PREFERRED EMBODIMENT

In the preferred practice of the invention, a specimen suspected of containing Candida is mixed with a solution of potassium hydroxide and an indictor of the formula $$C_{30}H_{31}ClN_6$$

which is known as Janus Green B and is described as 3 (diethylamino)-7-[p-(dimetyhlamino)phenylazo]-5-phenylphenazinium chloride. Without being bound by any theories, it is believed that the Janus Green compound, when dissolved in an alkaline solution, forms a complex and is highly specific to phospholipid concentrations in the fungal bodies because its diethyldimethyl structure readily attaches to and becomes chemically bound with the lipid groups within the Candida bodies. The highly alkaline solution eliminates all other existing microbial bodies and solids. The following examples are demonstrative of specific test results.

EXAMPLE I

A 0.5 mM $C_{30}H_{31}ClN_6$ indicator solution was formed by dissolving Janus Green B in 2.5 ml of a 25% KOH solution in a conical-bottom centrifuge test tube. A 0.1 ml specimen taken from a cultured colony of Candida was introduced into the indicator solution and agitated by hand until no solids were visible (about 15 seconds). The solution was then centrifuged for five minutes. A dark purple precipitate was amassed in the lower tip of the test tube.

The precipitate was extricated and, under microscopic comparison, exhibited exact morphology with a control colony culture. The extracted precipitate was smeared onto Sabouraud and Nickerson medium and incubated for twenty-four hours. No colonization was observed, thus evidencing destruction of Candida activity.

EXAMPLE II

The procedure of Example I was duplicated using a 10% KOH solution. The observed results were essentially identical except that colonization of Candida was evident after incubation of the precipitate for twenty-four hours.

EXAMPLE III

The procedure of EXAMPLE I was duplicated using a 1.0 mM $C_{30}H_{31}ClN_6$ concentration of Janus Green B. The observed results were essentially identical except that the solution above the amassed precipitate exhibited slight coloration.

EXAMPLE IV

The procedure of EXAMPLE I was duplicated using a 0.1 ml vaginal secretion specimen known to contain infectious levels of Candida. The observed results were essentially identical.

EXAMPLE V

The procedure of EXAMPLE I was duplicated using a 1.0 ml vaginal secretion specimen from an infection-free candidate. No precipitate was formed. The test solution exhibited no discernible coloration.

EXAMPLE VI

The procedure of EXAMPLE I was duplicated using a 1.0 ml vaginal secretion specimen from an infection-free candidate and 1.0 mM $C_{30}H_{31}ClN_6$. No precipitate was formed but the solution exhibited a faint bluish coloration.

In addition to the foregoing specific examples, various tests were made to determine the effect of variations in concentration of the alkaline solution. It was discovered that the concentration of KOH could be varied from less than 5% to about 35% without appreciable effect on the rapidity of the staining or precipitation of Candida bodies. However, stained Candida precipitate taken from indicator solutions containing KOH concentrations of less than about 15% exhibited a definite tendency to produce viable colonies of yeast when incubated. Since clinical preference dictates destruction of infectious bodies in test procedures, the concentration of KOH should preferably be in the range of about 25% to 30%.

Potassium hydroxide has been demonstrated to be particularly useful as the alkaline solution. However, other solutions having a high degree of alkalinity (such as sodium hydroxide and the like) may be used in similar manner and produce similar results.

The Janus Green B compound appears to be a specific indicator for Candida as described above. Various tests using various solutions of other known biological indicators failed to produce any discernible marking of Candida yeast bodies.

The indicator solution of the invention may be prepared by simply adding a measured amount of water to a prepared dry mix of KOH and $C_{30}H_{31}ClN_6$ in appropriate amounts and proportions. Since the indicator solution is specific to Candida and produces essentially immediate visual results, the dry mix (or separate premeasured amounts of caustic and Janus Green B) may be marketed as a unit with simple instructions for either self-administered or physician/technician-administered applications. The test results are not only specific, but essentially immediately available and produce nothing more than a disposable caustic solution containing dead yeast bodies. The invention thus provides an inexpensive, safe and rapid means for detecting the presence of Candida and an indication of the relative infection level thereof.

Although the invention has been described herein with particular reference to specific embodiments thereof, it is to be understood that the forms described in detail are to be taken as preferred embodiments. Various changes, modifications, combinations and variations may be resorted to without departing form the spirit and scope of the invention as defined by the appended claims.

What is claimed:

1. The method of determining the presence of Candida comprising the steps of:
    (a) collecting a specimen suspected of containing Candida yeast bodies;
    (b) introducing the suspect specimen into an alkaline solution containing an indicator represented by the formula $$C_{30}H_{31}ClN_6$$

wherein said indicator is a compound described as 3 (diethylamino)-7-[p-(dimetyhlamino)phenylazo]-5phenylphenazinium chloride; and
    (c) detecting the presence of a colored precipitate in the solution.

2. The method set forth in claim 1 wherein said alkaline solution is prepared by dissolving potassium hydroxide in water.

3. The method set forth in claim 2 wherein said alkaline solution is about 5% to about 35% potassium hydroxide.

4. The method set forth in claim 1 wherein the concentration of said compound is about 0.5 mM to about 1.0 mM $C_{30}H_{31}ClN_6$.

5. The method set forth in claim 4 wherein said alkaline solution is from about 25% to about 30% potassium hydroxide.

6. The method set forth in claim 1 including the step of agitating the solution after introduction of the suspect specimen.

7. The method set forth in claim 1 including the step of centrifuging the solution after introduction of the suspect specimen.

* * * * *

UNITED STATES PATENT AND TRADEMARK OFFICE
CERTIFICATE OF CORRECTION

PATENT NO. : 5,372,935

DATED : December 13, 1994

INVENTOR(S) : Charles L. Capps

It is certified that error appears in the above-identified patent and that said Letters Patent is hereby corrected as shown below:

Col. 4, line 27, insert a hyphen (-) between "5" and "phenylphenazinium"

Signed and Sealed this

Ninth Day of May, 1995

BRUCE LEHMAN

*Attest:*

*Attesting Officer*        *Commissioner of Patents and Trademarks*

UNITED STATES PATENT AND TRADEMARK OFFICE
CERTIFICATE OF CORRECTION

PATENT NO.  : 5,372,935
DATED       : December 13, 1994
INVENTOR(S) : Charles L. Capps It is certified that error appears in the above-identified patent and that said Letters Patent is hereby corrected as shown below:

Col. 1, line 14, delete the period (.)

Col. 4, line 27, insert a hyphen (-) between "5" and "phenylphenazinium"

This certificate supersedes Certificate of Correction issued May 9, 1995.

Signed and Sealed this

Twentieth Day of June, 1995

Attest:

BRUCE LEHMAN

*Attesting Officer*          *Commissioner of Patents and Trademarks*